US005591128A

United States Patent [19]

Sithole

[11] Patent Number: 5,591,128

[45] Date of Patent: Jan. 7, 1997

[54] GASTROSTOMY TUBE

[76] Inventor: Deborah I. Sithole, 241-20 Northern Blvd.; Apt. 6C, Douglaston, N.Y. 11362

[21] Appl. No.: 397,916

[22] Filed: Mar. 3, 1995

[51] Int. Cl.[6] .................. A61M 25/00

[52] U.S. Cl. .................. 604/96; 604/284; 606/192

[58] Field of Search .................. 604/96, 43, 97, 604/284, 117, 103, 99; 606/192, 195, 194

[56] References Cited

U.S. PATENT DOCUMENTS

| | | | |
|---|---|---|---|
| 3,394,705 | 7/1968 | Abramson | 604/43 |
| 3,834,394 | 9/1974 | Hunter et al. | 604/99 X |
| 4,607,635 | 8/1986 | Heyden | 128/207.15 |
| 4,685,901 | 8/1987 | Parks | 604/96 |
| 5,000,743 | 3/1991 | Patel | 606/194 |
| 5,024,655 | 6/1991 | Freeman et al. | 604/53 |
| 5,071,405 | 12/1991 | Piontek et al. | 604/96 |
| 5,143,062 | 9/1992 | Peckham | 604/43 X |
| 5,239,982 | 8/1993 | Trauthen | 604/117 X |
| 5,279,567 | 1/1994 | Ciaglia et al. | 604/117 |
| 5,353,787 | 10/1994 | Price | 604/117 X |
| 5,358,488 | 10/1994 | Suriyapa | 604/96 |
| 5,360,401 | 11/1994 | Turnland | 604/96 |
| 5,462,528 | 10/1995 | Roewer | 604/96 |

*Primary Examiner*—Randall L. Green
*Assistant Examiner*—V. Alexander
*Attorney, Agent, or Firm*—Michael I. Kroll

[57] ABSTRACT

An improved gastrostomy tube comprising a main conduit having a slanted outlet port at a lower end. A balloon is affixed to the lower end of the main conduit and about the slanted outlet port. A valve stem is connected at an angle to an upper end of the main conduit. A one-way valve is affixed to an upper end of the valve stem. An elongated filler pipe extends from the one-way valve through the valve stem and down through a wall of said main conduit into the balloon. A fluid, such as a saline solution/air, can be forced through the one-way valve and the elongated filler pipe, to inflate the balloon into a kidney shape, thereby making it easier and safer to insert the lower end of the main conduit through an opening in a stomach from an opening in an external surface of a body of a person.

3 Claims, 2 Drawing Sheets

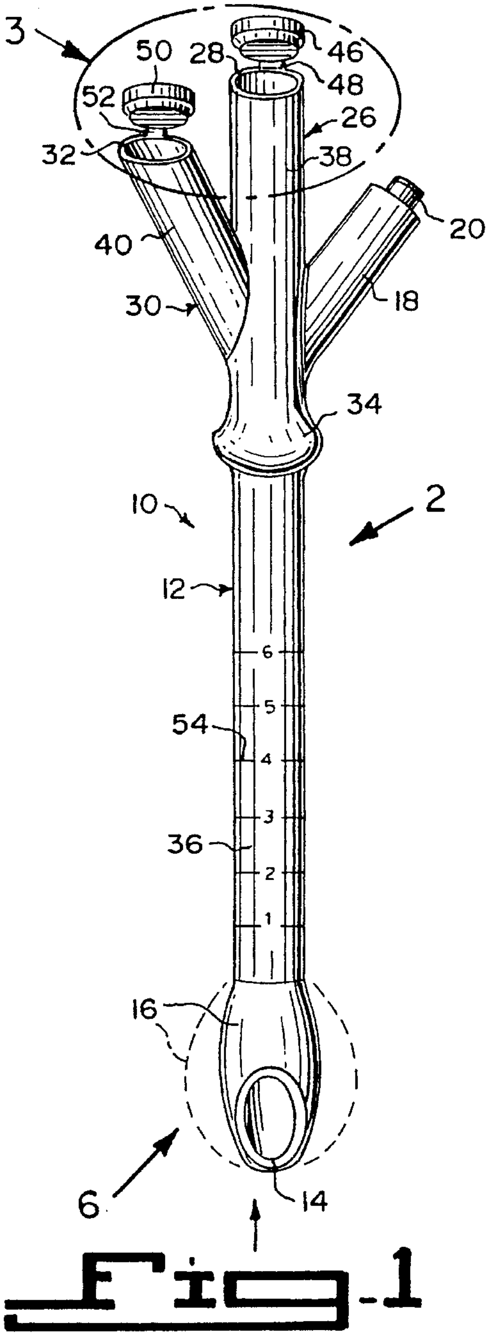
Fig-1
Fig-2
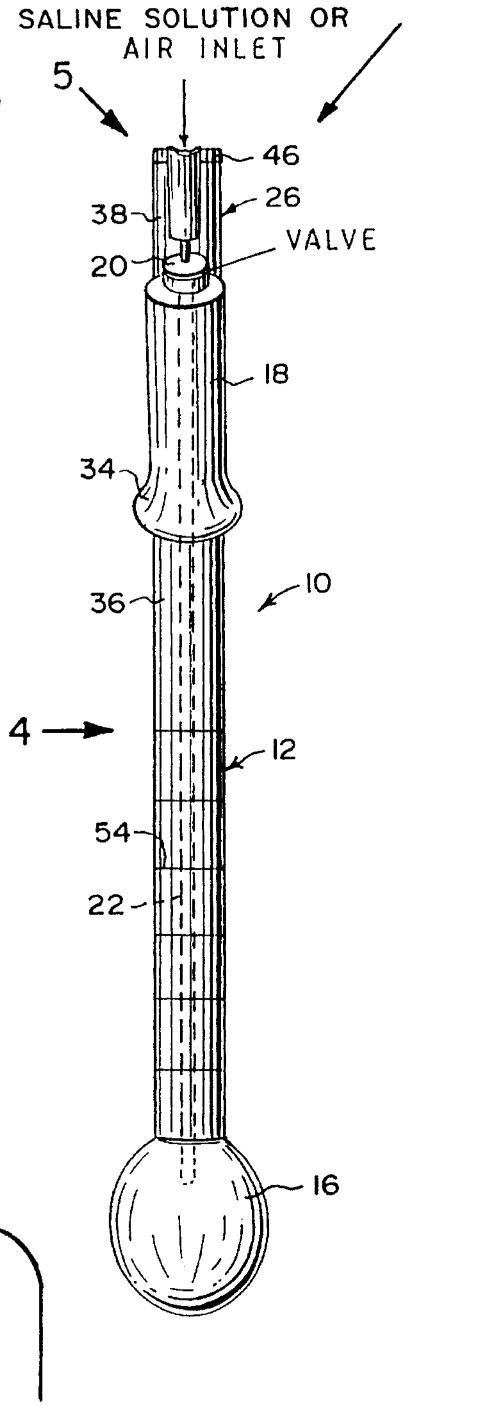
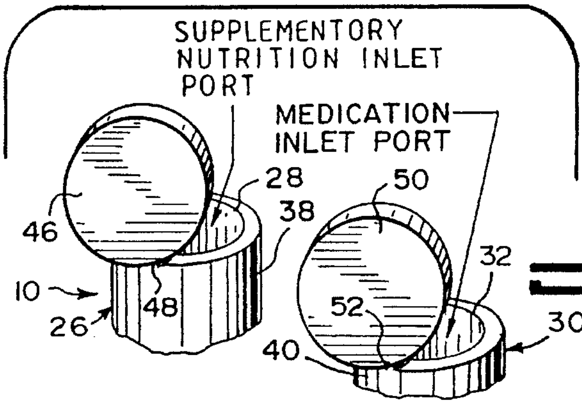
Fig-3

GASTROSTOMY TUBE

BACKGROUND OF THE INVENTION

1. Field of the Invention

The instant invention relates generally to medical instruments and more specifically it relates to an improved gastrostomy tube.

2. Description of the Prior Art

Numerous medical instruments have been provided in prior art that are adapted to assist doctors in examining and treating patients. While these units may be suitable for the particular purpose to which they address, they would not be as suitable for the purposes of the present invention as heretofore described.

SUMMARY OF THE INVENTION

The instant invention is an improved gastrostomy tube with a slanted outlet port, which becomes more kidney shaped once a balloon about the slanted outlet port is inflated. Many patients in nursing homes and hospitals are using gastrostomy tubes in order to provide supplementary nutrition. This tube has three conduits, in which primary and secondary conduits are connected to a main conduit. A valve stem also connected to the main conduit has a one-way valve, in which water or air can be used to inflate the balloon located at the slanted outlet port of the main conduit. Because of the kidney shape at the slanted outlet port, when the balloon is inflated it is gentler and does not irritate the stomach; also, it does not have a hard lower end, which are on other gastrostomy tubes.

A primary object of the present invention is to provide an improved gastrostomy tube that will overcome the shortcomings of the prior art devices.

Another object is to provide an improved gastrostomy tube, that will help prevent or limit muscosal irritation in the stomach, which may lead to gastrointestinal bleeding to people who have to have the gastrostomy tube inserted into the stomach from the external surface of the body, to provide nutrition.

An additional object is to provide an improved gastrostomy tube that is easier to insert into the stomach, because its slanted outlet port will become rounder and less visible once a balloon at its lower end is inflated.

A further object is to provide an improved gastrostomy tube that is simple and easy to use.

A still further object is to provide an improved gastrostomy tube that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views, and wherein:

FIG. 1 is a front perspective of the instant invention.

FIG. 2 is a side view taken in the direction of arrow 2 in FIG. 1.

FIG. 3 is an enlarged rear perspective view of a top portion thereof as indicated by arrow 3 in FIG. 1.

Similar reference characters denote corresponding features consistently throughout the attached drawings.

DETAILED DESCRIPTION OF THE PREFERRED EMBODIMENTS

Figure 4:
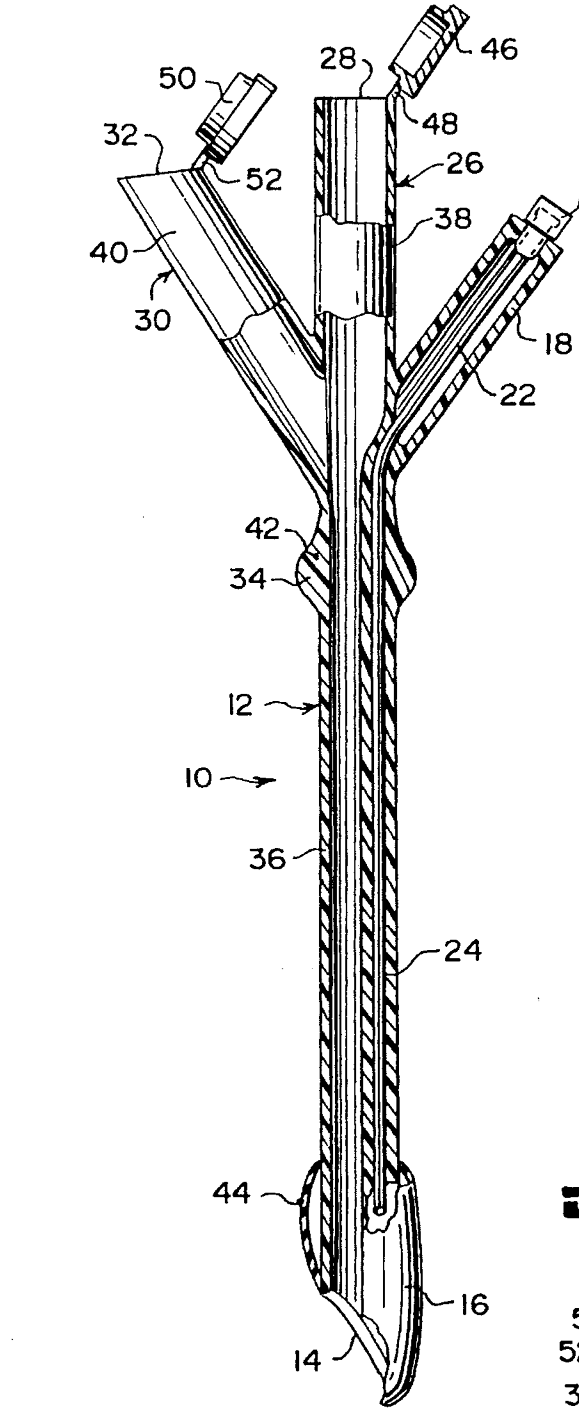
FIG. 4 is a front view taken in the direction of arrow 4 in FIG. 3, with parts broken away and in section.
Figure 6:
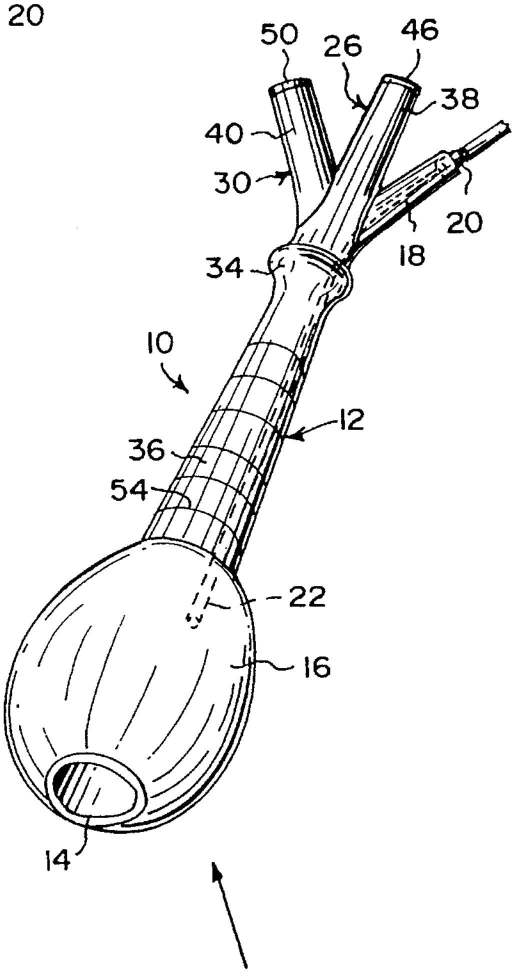
FIG. 6 is a bottom front perspective view taken in the direction of arrow 6 in FIG. 1.
Figure 5:
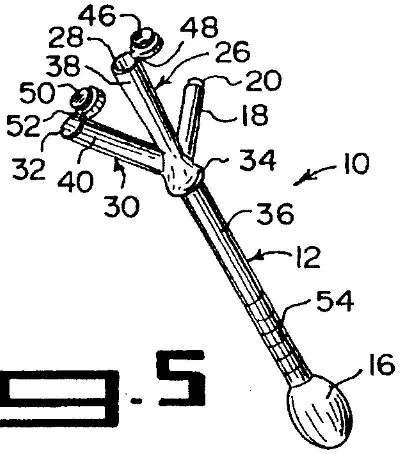
FIG. 5 is a top front perspective view taken in the direction of arrow 5 in FIG. 2.

Turning now descriptively to the drawings, in which similar reference characters denote similar elements throughout the several views, FIGS. 1 through 5 illustrate an improved gastrostomy tube 10, comprising a main conduit 12 having a slanted outlet port 14 at a lower end. A balloon 16 is affixed to the lower end of the main conduit 12 and about the slanted outlet port 14. A valve stem 18 is connected at an angle to an upper end of the main conduit 12. A one-way valve 20 is affixed to an upper end of the valve stem 18. An elongated filler pipe 22 extends from the one-way valve 20 through the valve stem 18 and down through a wall 24 of the main conduit 12 into the balloon 16. A fluid, such as a saline solution/air, can be forced through the one-way valve 20 and the elongated filler pipe 22, to inflate the balloon 16 into a kidney shape thereby making it easier and safer to insert the lower end of the main conduit 12, through an opening in a stomach from an opening in an external surface of a body of a person.

A primary conduit 26, has an inlet port 28 at an upper end and is fluidly connected longitudinally with the upper end of the main conduit 12. Supplementary nutrition can be inserted into the inlet port 28 of the primary conduit 26, to travel through the main conduit 12, out of the slanted outlet port 14 and into the stomach of the person.

A secondary conduit 30, having an inlet port 32 at an upper end and is fluidly connected at an angle with the upper end of the main conduit 12. Medication can be inserted into the inlet port 32 of the secondary conduit 30, to travel through the main conduit 12, out of the slanted outlet port 14 and into the stomach of the person. A finger grip stop member 34 is about the upper end of the main conduit 12 and directly below a juncture of the valve stem 18, the primary conduit 26 and the secondary conduit 30.

The main conduit 12 is a hollow cylindrical trunk channel 36. The primary conduit 26 is a hollow cylindrical upright channel 38. The secondary conduit 30 is a hollow cylindrical branch channel 40.

The hollow cylindrical trunk channel 36, the hollow cylindrical upright channel 38, the hollow cylindrical branch channel 40, the valve stem 18 and the finger grip stop member 34 are all integral to each other and fabricated out of a durable plastic material 42. The balloon 16 is fabricated out of a stretchable rubber material 44.

A first seal cap 46 is integrally hinged at 48 to the upper end of the hollow cylindrical upright channel 38. A second seal cap 50 is integrally hinged at 52 to the upper end of the hollow cylindrical branch channel 40. The first seal cap 46 and the second seal cap 50 are fabricated out of the durable plastic material 42. Scale markings 54 are along the hollow cylindrical trunk channel 36, to indicate the amount of supplementary nutrition and medication that can be inserted therein and to measure the safe placement of the tube above the inflated balloon in case a person has reverse peristalsis wherein the gastrostomy tube gets sucked into the stomach.

The inflatable balloon 16 can hold up to fifteen cubic centimeters of air or fluid (normal saline solution), depending upon the age and size of the person using it.

OPERATION OF THE INVENTION

To use the improved gastrostomy tube 10, the following steps should be taken:

1. Insert the slanted outlet port 14 of the main conduit 12 through the opening in the stomach from the opening in an external surface of a body of a person.

2. Force the fluid, such as saline solution/air, through the one-way valve 20 and the elongated filler pipe 22, to inflate the balloon 16 into a kidney shape.

3. Open the first seal cap 46.

4. Place the supplementary nutrition into the inlet port 28 of the primary conduit 26, so that it can travel through the main conduit 12 and out of the slanted outlet port 14 into the stomach of the person.

5. Close the first seat cap 46 when done.

6. Open the second seal cap 50.

7. Place the medication into the inlet port 32 of the secondary conduit 30, so that it can travel through the main conduit 12 and out of the slanted outlet port 14 into the stomach of the person.

8. Close the second seal cap 50 when done.

LIST OF REFERENCE NUMBERS

10 improved gastrostomy tube
12 main conduit of 10
14 slanted outlet port of 12
16 balloon at 14
18 valve stem on 12
20 one-way valve on 18
22 elongated filler pipe
24 wall of 12
26 primary conduit on 12
28 inlet port of 26
30 secondary conduit on 12
32 inlet port of 30
34 finger grip stop member
36 hollow cylindrical trunk channel for 12
38 hollow cylindrical upright channel for 26
40 hollow cylindrical branch channel for 30
42 durable plastic material of 36, 38, 40, 18 and 34
44 stretchable rubber material of 16
46 first seal cap
48 hinge of 46 on 38
50 second seal cap
52 hinge of 50 on 40
54 scale markings on 36

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. An improved gastrostomy tube comprising:
 a) a main conduit consisting of a hollow cylindrical upright channel having an upper end and a lower end with a slanted outlet port at said lower end;
 b) a balloon affixed to said lower end of said main conduit enclosing said slanted outlet port leaving said slanted outlet port within said balloon, said balloon being kidney shaped when inflated and having an opening aligned and coextensive with said slanted outlet port;
 c) a valve stem connected at an angle to said upper end of said main conduit:
 d) a one-way valve affixed to an upper end of said valve stem;
 e) an elongated filler pipe extending from said one-way valve through said valve stem and down through a wall of said main conduit into said balloon, so that a fluid can be forced through said one-way valve and said elongated filler pipe to inflate said balloon, thereby making it easier and safer to insert said lower end of said main conduit through an opening in a stomach from an opening in an external surface of a body of a person;
 f) a primary conduit consisting of a hollow cylindrical upright channel having an inlet port at one end and fluidly connected at the opposite end to said upper end of said main conduit to permit supplementary nutrition to be inserted into said inlet port of said primary conduit to travel through said main conduit and out of said slanted outlet port and into the stomach of the person;
 g) a secondary conduit consisting of a hollow cylindrical branch channel having an inlet port at one end and fluidly connected at the opposite end to the upper end of said main conduit to permit the insertion of medication into the inlet port of said secondary conduit to travel through said main conduit and out of said slanted outlet port and into the stomach of the person; and
 h) stop member means integrally formed in the outer surface of said main conduit directly below the juncture of said valve stem, said primary conduit, and said secondary conduit to provide a fixed finger grip on said gastrostomy tube.

2. An improved gastrostomy tube as recited in claim 1, wherein said main conduit, said primary conduit, said secondary conduit, said valve stem and said finger grip stop member are all integral to each other and fabricated out of a durable plastic material.

3. An improved gastrostomy tube as recited in claim 2, wherein said balloon is fabricated out of a stretchable rubber material.

* * * * *